US012778476B2

(12) United States Patent
Arfaoui et al.

(10) Patent No.: US 12,778,476 B2
(45) Date of Patent: Nov. 3, 2026

(54) EXPANDABLE ELECTRODE SET

(71) Applicant: BIOSERENITY MEDICAL DEVICES GROUP, Paris (FR)

(72) Inventors: Nadia Arfaoui, Chatou (FR); Alexandre Aristides, Paris (FR); Marc Frouin, Paris (FR); Philippe Guermonprez, Paris (FR); Ekin Koca, Paris (FR); Maylis Merchet, Paris (FR); Fabian Parizel, Paris (FR); Pierre Prot, Paris (FR)

(73) Assignee: Bioserenity Medical Devices Group, Paris (FR)

( * ) Notice: Subject to any disclaimer, the term of this patent is extended or adjusted under 35 U.S.C. 154(b) by 731 days.

(21) Appl. No.: 17/926,806

(22) PCT Filed: May 21, 2021

(86) PCT No.: PCT/EP2021/063681

§ 371 (c)(1),
(2) Date: Nov. 21, 2022

(87) PCT Pub. No.: WO2021/234156

PCT Pub. Date: Nov. 25, 2021

(65) Prior Publication Data

US 2023/0200699 A1 Jun. 29, 2023

Related U.S. Application Data

(63) Continuation of application No. 16/880,104, filed on May 21, 2020.

(30) Foreign Application Priority Data

Jul. 21, 2020 (TW) ................................ 109124603

(51) Int. Cl.
*A61B 5/256* (2021.01)
*A61B 5/24* (2021.01)
(Continued)

(52) U.S. Cl.
CPC ................ *A61B 5/24* (2021.01); *A61B 5/256* (2021.01); *A61B 5/0522* (2013.01);
(Continued)

(58) Field of Classification Search
CPC ......... A61B 5/271; A61B 5/273; A61B 5/291; A61B 5/6814; A61B 5/6823; A61B 5/6832
See application file for complete search history.

(56) References Cited

U.S. PATENT DOCUMENTS 5,293,867 A * 3/1994 Oommen ............ A61B 5/6841 600/383
8,019,402 B1 9/2011 Kryzpow et al.
(Continued)

FOREIGN PATENT DOCUMENTS

AU 6558101 A 10/2001
CN 104027106 A 9/2014
(Continued)

OTHER PUBLICATIONS

Office Action for U.S. Appl. No. 16/880,104, mailed on Jul. 1, 2024, Arfoui, "Expandable Electrode Set", 19 Pages.
(Continued)

*Primary Examiner* — Eun Hwa Kim
(74) *Attorney, Agent, or Firm* — Lee & Hayes, P.C.

(57) ABSTRACT

An expandable electrode set, methods of using the expanding electrode set, electrode set systems, and methods of manufacturing an electrode set. Various examples of an electrode set include nodes that are physically connected to each other by connectors that have a shape that allows for
(Continued)

the deformation of the electrode set. The shape and material of the connectors is designed to provide a consistent deformation so that, when placing alignment markers on a part of a body to be monitored, the nodes end up in correct locations on the part of the body for the measurement being performed. The electrode set may include sensors, emitters, or sensors and emitters in various configurations.

10 Claims, 8 Drawing Sheets

(51) Int. Cl.
*A61B 5/0522* (2021.01)
*A61B 5/0536* (2021.01)

(52) U.S. Cl.
CPC ....... *A61B 5/0536* (2013.01); *A61B 2562/164* (2013.01); *A61B 2562/227* (2013.01)

(56) References Cited

U.S. PATENT DOCUMENTS

| | | | | |
|---|---|---|---|---|
| 2008/0177168 | A1* | 7/2008 | Callahan | A61B 5/6841 600/382 |
| 2011/0270100 | A1 | 11/2011 | Chang | |
| 2013/0281814 | A1 | 10/2013 | Tilt et al. | |
| 2014/0257073 | A1* | 9/2014 | Machon | A61B 5/6803 600/383 |
| 2015/0011857 | A1* | 1/2015 | Henson | B32B 37/24 600/383 |
| 2017/0019988 | A1 | 1/2017 | McGrane et al. | |
| 2017/0164861 | A1* | 6/2017 | Cahan | A61B 5/291 |
| 2018/0271444 | A1* | 9/2018 | Floyd | A61B 5/291 |
| 2019/0313930 | A1 | 10/2019 | Hayes-Gill et al. | |
| 2021/0361184 | A1 | 11/2021 | Arfaoui et al. | |

FOREIGN PATENT DOCUMENTS

| | | | |
|---|---|---|---|
| CN | 105992564 | A | 10/2016 |
| CN | 108024721 | A | 5/2018 |
| CN | 110338808 | A | 10/2019 |
| CN | 110573065 | A | 12/2019 |
| EP | 2105089 | A1 | 9/2009 |
| EP | 2654556 | B1 | 10/2018 |
| JP | 2017035174 | A | 2/2017 |
| JP | 2017113088 | A | 6/2017 |
| TW | 201316950 | A | 5/2013 |
| TW | 201701823 | A | 1/2017 |
| TW | 201832720 | A | 9/2018 |

OTHER PUBLICATIONS

International Search Report issued on Sep. 1, 2021, in corresponding International Application No. PCT/EP2021/063681, 4 pages.
Translated Office Action for Japanese Application No. 2022-570497, Dated Mar. 18, 2025, 5 pages.
Office Action for U.S. Appl. No. 16/880,104, Dated Feb. 28, 2025, 14 Pages.
Office Action for U.S. Appl. No. 16/880,104, mailed on Dec. 8, 2023, Nadia Arfaoui, "Expandable Electrode Set", 11 pages.
Taiwanese Office Action mailed on Feb. 20, 2021 for Taiwanese Patent Application No. 109124603, a counterpart of U.S. Appl. No. 16/880,104, 7 pages.
Office Action for U.S. Appl. No. 16/880,104, dated Jun. 20, 2025, 15 Pages.
U.S. Office Action for U.S. Appl. No. 16/880,104, mailed on May 1, 2023, Nadia Arfaoui, "Expandable Electrode Set", 9 pages.
Office Action for U.S. Appl. No. 16/880,104, dated Mar. 24, 2026, 17 Pages.

* cited by examiner

EXPANDABLE ELECTRODE SET

FIELD

The present invention pertains to the field of the systems and methods for acquiring a physiological signal from a subject. In particular, the invention relates to a set of electrodes for measuring electrical physiological signal.

BACKGROUND

Acquiring electrophysiological signals is of great importance in current medical technologies. Electrical activity of heart (electrocardiogram ECG), brain (electroencephalogram EEG), nerves (electromyogram EMG) or pregnant women (fetus electrocardiogram or fECG) or other electrical measurement (electrooculography (EOG) for eyes, ERG EEG for intestine activities, and the like) are commonly recorded for diagnostic or monitoring purpose. In addition, stimulation by electric signals or imaging based on impedance measurements of a part of the body of a subject (EIT: electrical impedance tomography) are spreading quickly in medical practice. Achieving correct measurements of electrophysiological signals requires to locate precisely measuring electrodes. Correct placement of electrodes for stimulation or imaging is necessary for accurate readings.

Similarly, when a given pathology required co deployment of electrodes (or other sensors) with specific placement and other type of skin contact sensors like light emitting diodes and photoreceptors or sensors created using Silicon integrated cells (MEMS) it is required for correct measurement to reach correct positions precisions in many medical cases.

SUMMARY

This invention thus relates to an electrode set, comprising:

a first node and a second node, the first node comprising a first pad for receiving electromagnetic energy from a first portion of a part being studied, the second node comprising a second pad;

a connector connecting the first node to the second node, the connector formed from a shape that provides for a consistent deformation from a first distance between the first node and the second node to one or more second distances between the first node and the second node as a pull force is applied to the first node or the second node, wherein in an undeformed state the first node and the second node are planar and in a deformed state the first node and the second node are non-planar, wherein a length of the connector remains constant from the undeformed state to the deformed state;

at least one alignment marker affixed to either the first node or the second node, the at least one alignment marker to be removably affixed to a landmark on the subject of the part being studied, wherein the at least one alignment marker is configured to transfer the pull force to either the first node or the second node as the alignment marker is being affixed to the landmark.

The wording of connector formed from a shape that provides for a consistent deformation, may also be understood as connector having a shape configured to provide a consistent deformation. Advantageously, the present electrode set when it is in its undeformed state is planar which allow for compact storage of a large number of electrode sets. This aspect is particularly interesting for example for ambulances where a large number of different medical system/devices has to be stored for moving around.

According to one embodiment, the second pad for receiving electromagnetic energy from a second portion of the part being studied or for sending a signal into the first portion of a part being studied According to one embodiment, the electrode set further comprises a first wire within the connector, the first wire in electrical communication with the first pad of the first node and extending to a measurement lead.

According to one embodiment, the electrode set further comprises a second wire within the connector, the second wire having in electrical communication with the second pad of the second node and extending to the measurement lead, wherein the measurement lead terminates at a measurement connector to be inserted into a monitoring/input device.

According to one embodiment, the electrode set further comprises a plurality of third nodes, at least a portion of the plurality of third nodes comprising a pad for receiving electromagnetic energy from a plurality of third portions of the part being studied; and a plurality of second connectors connecting at least one of the plurality of third nodes to either the first node or the second node, the plurality of second connectors formed from the shape that provides for consistent deformation from a first distance between at least a portion of the plurality of third nodes to one or more second distances between at least a portion of the plurality of third nodes as a pull force is applied to the at least one alignment marker, wherein in an undeformed state the plurality of third nodes are planar and in a deformed state the plurality of third nodes are non-planar.

According to one embodiment, the electrode set further comprises a plurality of second alignment markers affixed to one or more of the plurality of third nodes, the plurality of second alignment markers to be removably affixed to a plurality of second landmarks on the subject of the part being studied, wherein the plurality of second alignment markers are configured to transfer the pull force to at least a portion of the plurality of third nodes as the plurality of second alignment markers are being affixed to the landmark.

According to one embodiment, the electrode set further comprises a pad stiffener affixed to the first node, wherein the pad stiffener secures an electrical connection between the pad and the first wire.

According to one embodiment, the connector comprises a plastic substrate, polyimide, polyethylene, polyether ether ketone (PEEK), or a non-conductive polyester or polymer.

According to one embodiment, the shape comprises a sinusoidal shape. This embodiment, advantageously allows the spacing between the nodes to be changed from a first distance to one or more second distances depending on how much the connectors are pulled.

According to one embodiment, the shape comprises a spiral, a double spiral, a horseshoe, or an angular shape.

According to one embodiment, the first pad and/or the second pad comprises conductive or semi-conductive materials.

According to one embodiment, the first pad and/or the second pad comprises copper, aluminum, stainless steel, gold, silver, or alloys thereof.

According to one embodiment, the first wire and/or the second wire comprises copper, aluminum, stainless steel, gold, silver, or alloys thereof.

According to one embodiment, the first pad comprises a first passing hole and the second pad comprises a second passing hole, the first passing hole and the second passing hole being openings that allow for an injection of an electroconductive material enhancing electrical contact with skin.

According to one embodiment, the electrode set further comprises a third node, wherein the third node comprises a third pad to transmit electromagnetic energy.

According to one embodiment, the electromagnetic energy is near infrared light, infrared light, or visible light.

According to one embodiment, the electrode set further comprises a fourth node, wherein the fourth node comprises a fourth pad to receive electromagnetic energy resulting from the electromagnetic transmission from the third pad.

According to one embodiment, the electrode set further comprises a third node for receiving a sensor.

The present invention also relates to a method of measuring signals of a part of a subject, the method comprising:

- placing an electrode set proximate to the part to be measured, the electrode set comprising:
- a first node and a second node, the first node comprising a first pad for receiving electromagnetic energy from a first portion of a part being studied, the second node comprising a second pad for receiving electromagnetic energy from a second portion of the part being studied;
- a connector connecting the first node to the second node, the connector formed from a shape that provides for a consistent deformation from a first distance between the first node and the second node to one or more second distances between the first node and the second node as a pull force is applied to the first node or the second node, wherein in an undeformed state the first node and the second node are planar and in a deformed state the first node and the second node are non-planar, wherein a length of the connector remains constant from the undeformed state to the deformed state;
- at least one alignment marker affixed to either the first node or the second node, the at least one alignment marker to be removably affixed to a landmark on the subject of the part being studied, wherein the at least one alignment marker is configured to transfer the pull force to either the first node or the second node as the alignment marker is being affixed to the landmark;
- a first wire within the connector, the first wire in electrical communication with the first pad of the first node and extending to a measurement lead; and
- a second wire within the connector, the second wire having in electrical communication with the second pad of the second node and extending to the measurement lead, wherein the measurement lead terminates at a measurement connector to be inserted into a monitoring/input device:
  - affixing the at least one alignment marker to the landmark;
  - connecting the measurement lead to a monitoring/input device; and
  - instantiating a monitoring application in the monitoring/input device to commence measuring the electrophysiological signals of the part of the subject.

According to one embodiment, the method further comprises injecting an electroconductive, sonic, or light transmitting material through a first passing hole of the first pad and a second passing hold of the second pad.

According to one embodiment, the connector comprises a plastic substrate, polyimide, polyethylene, polyether ether ketone (PEEK), or a non-conductive polyester or polymer.

According to one embodiment, the shape comprises a sinusoidal shape.

According to one embodiment, the shape comprises a spiral, a double spiral, a horseshoe, or an angular shape.

According to one embodiment, the first pad and/or the second pad comprises conductive or semi-conductive materials.

According to one embodiment, the first pad and/or the second pad comprises copper, aluminum, stainless steel, gold, silver, or alloys thereof.

The present invention relates as well to a sensor set system comprising:

- a sensor set (100) according to any one of the embodiments cited above, wherein the monitoring/input device is configured to receive data of electrophysiological signals received from the first pad or the second pad; and
- a monitoring service in communication with the monitoring/input device for receiving the data of the electrophysiological signals or transmitting instructions to the monitoring/input device.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Examples of the present disclosure can comprise systems and methods for providing and using an expandable sensor set. When using a conventional sensor set to measure three-dimensional body parts, it is often difficult to properly align the sensors at the correct position on the body (part) of a patient to try to get as accurate of a reading as possible. This often limits the use of conventional sensor sets to hospitals or other facilities in which a technician is available for the installation. Because of the need for specialists to install conventional sensor sets, the costs to use conventional sensor sets can be prohibitively expensive as well as inconvenient, this in turns create limited capacities to leverage the data that can be acquired in many medical cases. It should be noted that, while some of the figures are described in terms of installation onto a subject by a second person, the presently disclosed subject matter is not limited in that manner, as various examples of the presently disclosed subject matter may be installed by the subject themselves.

Figure 1:
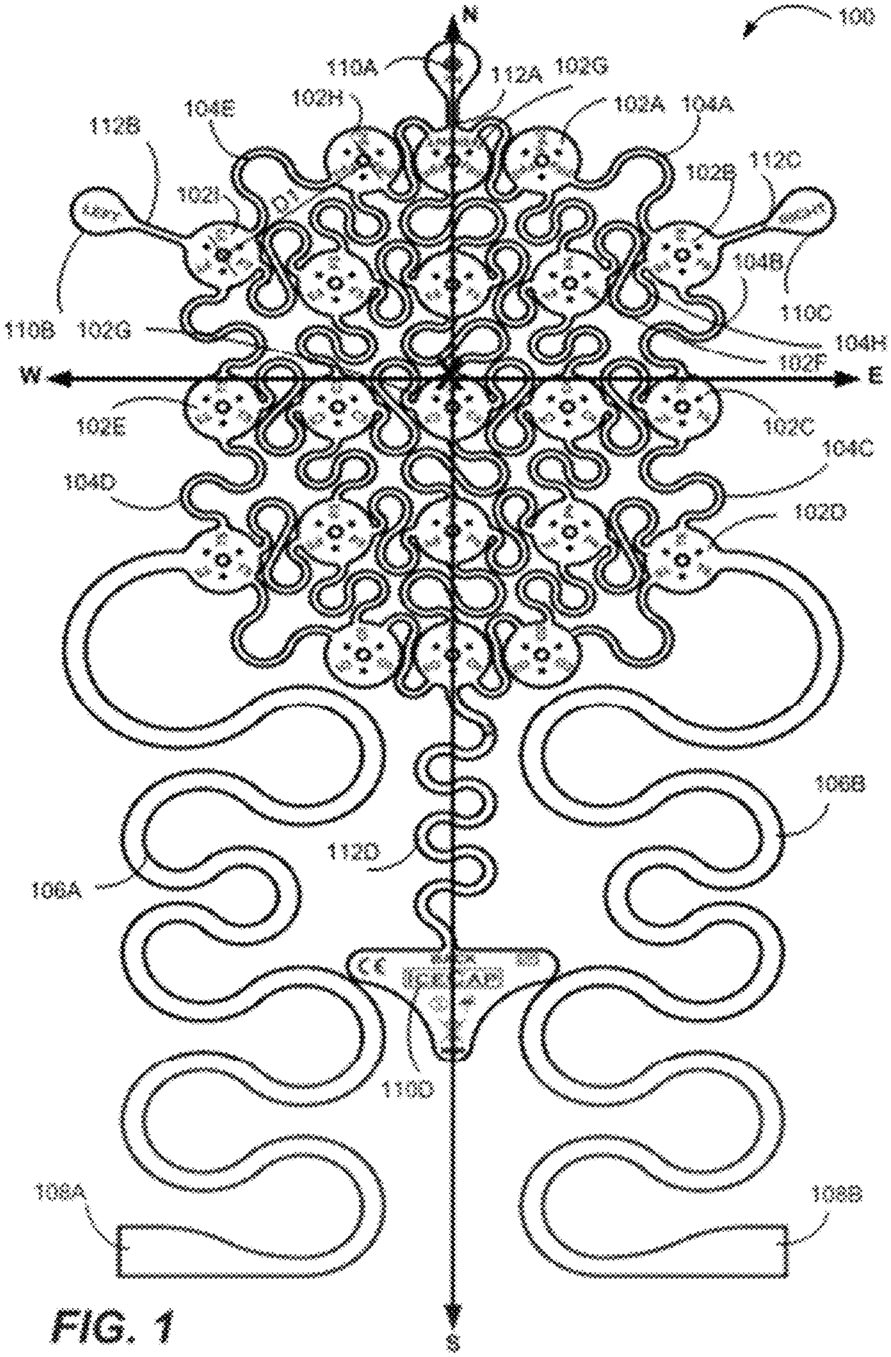
FIG. 1 depicts an expandable electrode set in a non-deployed state, in accordance with some examples of the present disclosure.
Figure 2:
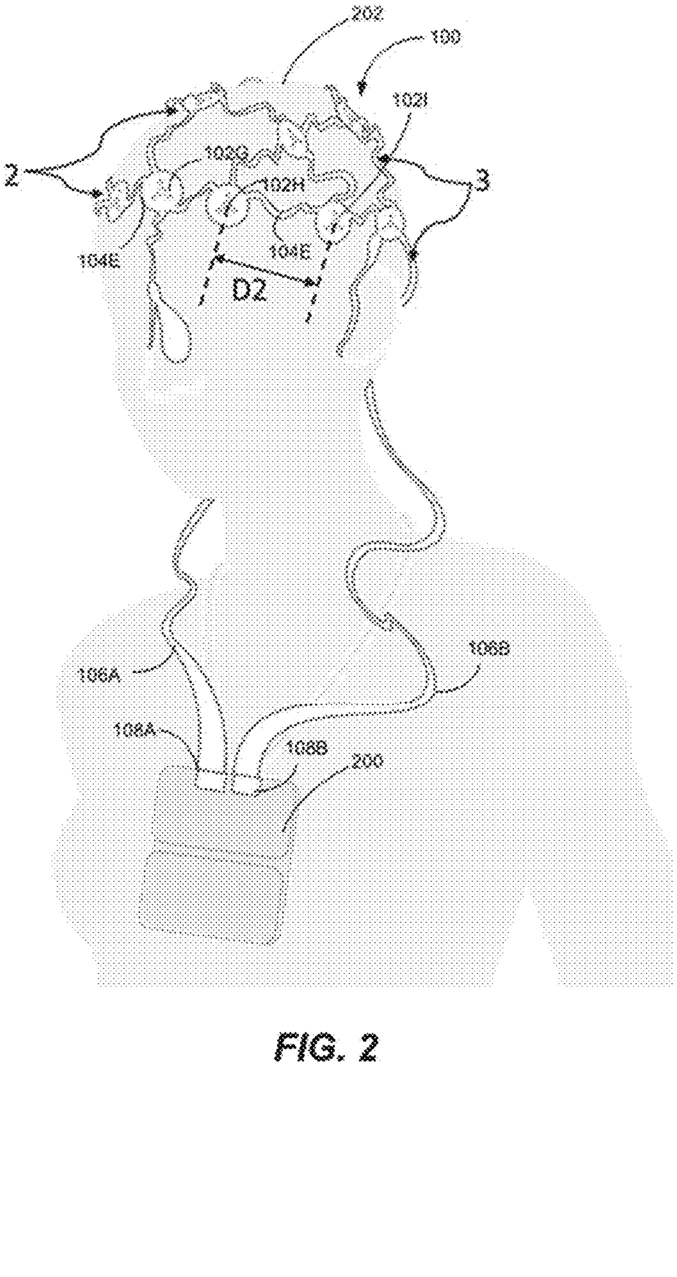
FIG. 2 depicts an electrode set in a deployed state, in accordance with some examples of the present disclosure

FIG. 1 depicts a top-down view of an expandable electrode set 100 in a non-deployed state. It should be noted that although some of the description herein is described in terms of an "electrode" or an "electrode set," the presently disclosed subject matter is not limited to electrodes, as the description using electrodes is merely exemplary and illustrative. As used herein, "non-deployed or undeployed" means that the electrode set 100 is not installed on a body part and "deployed" means that the electrode set 100 is partially or fully installed on a body part. Referring to FIG. 2, the electrode set 100 is shown in a deployed state. In the non-deployed state illustrated in FIG. 1, the electrode set 100 is substantially flat, meaning that when placed on a flat surface, all or substantially all of a bottom surface of the electrode set 100 proximate to the flat surface will be in contact with the surface. In the deployed state illustrated in FIG. 2, the electrode set 100 is partially deformed to wrap around a 3D body part of a patient or subject to be studied. In some examples, the deformation may be termed "warping," wherein both terms are interchangeable. For example, nodes 102H and 102I, connected by connector 104E, are shown in FIG. 1 to have a distance of D1 between the nodes 102I and 102H, whereas in FIG. 2, the distance between the nodes 102I and 102H is illustrated as D2, which is greater than D1.

Referring back to FIG. 1, the electrode set 100 includes nodes 102A-102F (collectively referred to herein as the "nodes 102," and individually the "node 102A," the "node 102B," and so forth) and connectors 104A-104E (collectively referred to herein as the "connectors 104," and individually the "connector 104A," the "connector 104B," and so forth). It is noted that FIG. 1 includes additional nodes and connectors not labeled, which is merely for purposes of illustration. The internal construction of the nodes 102 and the connectors 104 are described in more detail in FIGS. 3 and 4. In use, the nodes 102 are used to sense (measure or detect) electrophysiological signals that are the result of electrical activity of a particular body part. It is noted that the shapes of the various components of the electrode set 100 illustrated in FIG. 1 are merely exemplary and may have different shapes depending on a particular use. For example, the nodes 102 may be circular as illustrated in FIG. 1, but may also be ellipses, egg-shaped, squares, rectangles, and/or polygons, or combinations thereof. In some examples, the nodes 102 may be used to impart a current into the subject being tested to measure impedance. These and other uses of the nodes 102 as electro- or electromagnetic devices are considered to be within the scope of the presently disclosed subject matter.

The electrode set 100 further includes measurement leads 106A and 106B and measurement connectors 108A and 108B. The measurement leads 106A and 106B receive electrical signals from the nodes 102 through the connectors 104. The measurement leads 106A and 106B have within them wires from each of the nodes 102 that run from the nodes 102 to the measurement leads 106A and 106B. The measurement leads 106A and 106B are connected to a device that measures the electrical signals from the nodes 102 (shown in more detail in FIG. 2).

As noted above, in conventional electrode sets, a technician or other qualified individual is often required in order to ensure that the electrode set is properly positioned on a body part. The reason for this is that the nodes that measure bodily electrical activity need to be placed at certain points on the body to get as accurate of a reading as possible. The electrode set 100 of FIG. 1 provides various mechanisms that allow various users, including untrained people, to properly place the electrode set 100 on a body party (e.g. a head or a belly of a pregnant woman).

A first mechanism that allows for the proper placement of the electrode set 100 on a body part are alignment markers 110A-110D (collectively referred to herein as the "alignment markers 110," and individually the "alignment marker 110A," the "alignment marker 110B," and so forth). The alignment markers 110 are used by a person installing the electrode set 100 to properly align the electrode set 100. The alignment markers 110 are configured to be put in contact with a predefined anatomical landmark on a person to be studied. The landmarks can be based on various factors, including standards defined by a medical community to place the nodes 102 so as to record correctly electrophysiological signals. Such systems exist for ECG, EEG, EMG, and/or fECG or other electrical physiological signal as well as placement of other sensors sources for other measurement technologies. However, the presently disclosed subject matter does not require the use of specific landmarks, as other locations on a body may be used and are considered to be within the scope of the presently disclosed subject matter. For example, the ears, nose, belly button, or other landmark may be used for the proper placement of the electrode set 100. It should also be noted that the electrode set 100 is not limited to use on humans, as the electrode set 100 may be used on non-human subjects. In the example illustrated in FIG. 1, the alignment markers 110 are located according to nasion, inion and both tragi anatomical landmarks in the international 10-20 system or variants thereof, though as mentioned herein, other landmarks may be used and are considered to be within the scope of the presently disclosed subject matter.

A person installing the electrode set 100 places and temporarily affixes (using tape or other adhesive appropriate for use on a body) the one or more alignment markers 110 on one or more locations (i.e. the anatomical landmarks). In the example illustrated in FIG. 1, there are four alignment markers 110, although as previously mentioned, there may be more than four or fewer than four depending on the particular configuration of the electrode set 100. When placing one of the alignment markers 110 on the anatomical landmark, the placement of the alignment marker 110 advantageously exerts a force on the node 102 closest to the alignment marker 110 through marker connectors 112A-112D (collectively referred to herein as the "marker connectors 112," and individually the "marker connector 112A," the "marker connector 112B," and so forth). In one advantageous example, the placement of the alignment marker 110C exerts a pulling force on the node 102B through the marker connector 112C in a direction generally in line with force vector XE. Similarly, the placement of the alignment marker 110A exerts a force generally in line with force vector XN, the placement of the alignment marker 110B exerts a force generally in line with force vector XW, and the placement of the alignment marker 110D exerts a force generally in line with force vector XS.

The action of the pulling of the electrode set 100 in the direction of two or more force vectors (such as XE, XN, XW, and XS) causes the electrode set 100 to warp or deform. As used herein, "warp" refers to a material that has been deformed from a planar state (as illustrated in FIG. 1) to a three-dimensional state (as illustrated by way of example in FIG. 2). The electrode set 100 is designed with materials that provide an appropriate stretch force that counters the pulling force to correctly align the nodes 102 onto the one or more anatomical landmarks. For example, an elastic force (i.e. the force that occurs when a deformed object tries to return to its original shape) that is too low may cause various nodes to be too easily pulled in a particular direction. In this example, the rigidity of the structure of the electrode set 100 and its nodes 102 and connectors 104 is insufficient to provide a controlled and specific deployment of the nodes 102 of the electrode set 100. In another example, if the rigidity of the structure of the electrode set 100 is too great, meaning the elastic force is relatively significant, the structure of the electrode set 100 may require heavy glues or adhesives to keep the alignment markers 110 in place and may place an undue strain on the material of the electrode set 100, among other disadvantages.

Thus, construction of the electrode set 100 and its components, especially the connectors 104, are designed to provide a balance between rigidity and flexibility. In the example illustrated in FIG. 1, a sinusoidal shape constructed with particular materials advantageously achieves this balance. It should be understood that the shapes and materials are examples, as other shapes and materials may be used. For example, other shapes such as spiral-shaped, double spiral-shaped, horseshoe-shaped or angular-shaped may be used. The shape of the connectors 104 of the electrode set is designed to allow for a planar configuration when not deployed while allowing for a non-planar configuration during use.

Advantageously, the sinusoidal shape also allows the spacing between the nodes 102 to be changed from a first distance to one or more second distances depending on how much the connectors 104 are pulled. The one or more second distances may be used to allow the electrode set 100 to be deployed in various uses. In one embodiment, the ratio of a first distance between two nodes linked by a connector, such as the nodes 102B and 102F connected by the connector 104H, in the deployed configuration and the distance between the same two nodes linked by the same connector element in the undeployed configuration is greater than 1.05, and in some examples, greater than the ratios of 1.05 and up to 2.0, though greater ratios may be achievable depending on the particular materials, dimensions, and the like.

Further, the sinusoidal shape along with the predetermined elastic force provided by the connectors 104 advantageously allow for the electrode set 100 to be used on various sizes and shapes of body parts. For example, the electrode set 100 may be used for skulls or abdomens, as well as differently shaped body parts, including those of various cultures and ethnicities. As the electrode set 100 is installed on a body part, the sinusoidal shape and the elastic force cause the electrode set 100 to deform in a predetermined manner. For example, as the electrode set 100 is deformed to fit over a body part, the elastic force and the sinusoidal shape cause the nodes 102 of the electrode set 100 to space apart at distances in the direction of the force vectors that allow for a proper placement of the nodes 102 on the locations of the body part to be measured. This means that when installed, the electrode set 100 will not have an area of nodes 102 that remain bunched together at or near pre-deformation distances and other nodes 102 that are spread too far apart at or near post-deformation distances. The consistent deformation across all force vectors allows the electrode set 100 to be used on various body sizes and shapes. During the process from the undeformed to the deformed state, the length of the connectors 104 remain the same, meaning the connectors 104 don't stretch, but rather, their shape changes from a sinusoidal to linear shape.

In some examples, the connectors 104 are constructed using a polyimide, polyethylene, polyether ether ketone (PEEK), or other fully or partially insulative polymer. In some examples, the connectors 104 (including any internal components such as copper tracks or wiring) preferably have a thickness within a range of 90 μm to 200 μm, a range of 100 μm to 170 μm, and in a more preferable configuration, a range of thickness from 118 μm to 122 μm. In some examples, the thickness of the connectors 104 is 120 μm with a tolerance of twenty percent (20%). It should be noted that the thickness of the connectors 104 may vary depending on the particular material used in order to provide a similar elastic force.

Referring back to FIG. 2, also illustrated is a monitoring/input device 200. In some examples, the monitoring/input device 200 provides the electrical power to allow the nodes 102 to be used to detect electrophysiological signals produced by the part 202 of the human being studied, e.g. the head illustrated by way of example in FIG. 2. In the example in which the nodes 102 are being used to image the part 202, the monitoring/input device 200 provides the electrical power through the measurement leads 106A and 106B to allow for the imaging. As illustrated, the measurement leads 106A and 106B are connected to the monitoring/input device 200 by the insertion of the measurement connectors 108A and 108B into appropriate ports (not shown) of the monitoring/input device 202. The monitoring/input device 200 may record data for later transfer to a system for diagnosis/measurement and/or may have internal communication capabilities that allow the monitoring/input device 200 to transmit the data for use (explained in more detail in FIG. 5).

Figure 3:
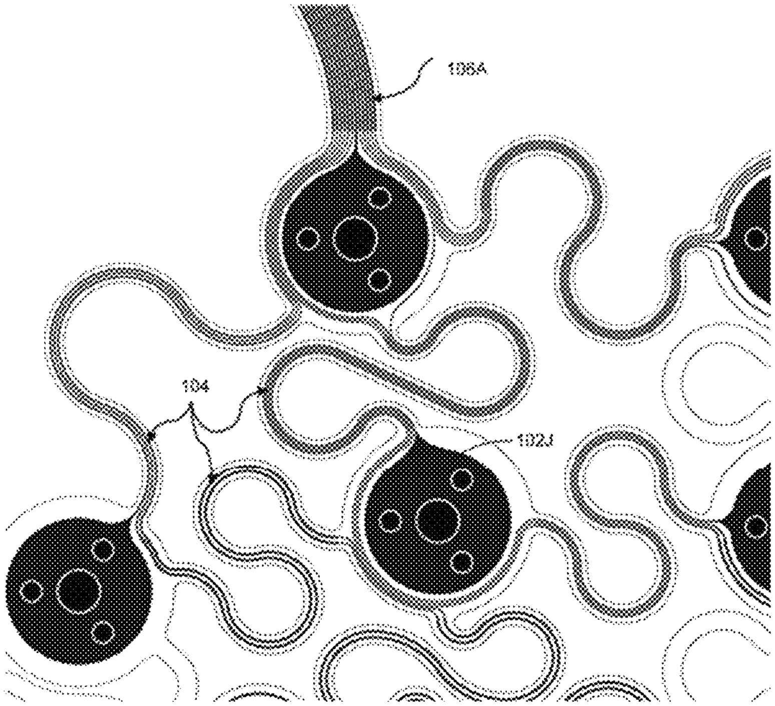
FIG. 3 illustrates electrical wiring in an expandable electrode set, in accordance with some examples of the present disclosure.

FIG. 3 illustrates electrical wiring in the electrode set 100, in accordance with some examples of the present disclosure. Shown in FIG. 3 are the measurement lead 106A and nodes 104. Within the nodes 104 and the measurement lead 106A (measurement lead 106B is similarly constructed) are wires that put the nodes 102 (for example, the node 102J in FIG. 3) in electrical communication with the measurement lead 106A, illustrated in more detail in FIG. 4.

Figure 4:
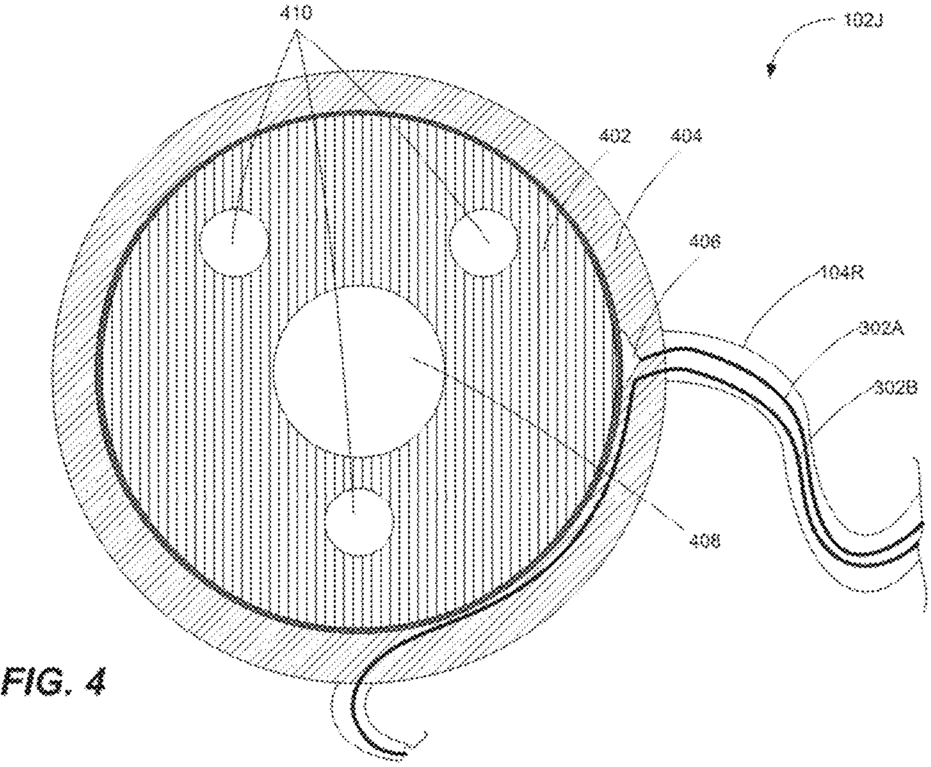
FIG. 4 is a close-up view of an example node used in an expandable electrode set, in accordance with some examples of the present disclosure.

FIG. 4 is a close-up view of the node 102J used in the electrode set 100, in accordance with some examples of the present disclosure. The node illustrated in FIG. 4 includes a pad 402, a pad stabilizer 404, and a pad stiffener 406. The pad 402 can be constructed of various conductive and semi-conductive materials including, but not limited to, copper, aluminum, stainless steel, and the like. An active area of the pad 402 (i.e. the area placed in contact or proximate to the surface of the part of the subject being studied) can comprise silver, silver chloride, electrically conductive silicone, electrically conductive polymer, or a plastic loaded with a conductive material such as carbon. The pad 402 is illustrated as being circular in shape, but other shapes, such as, but not limited to, a spiral, a double spiral, a horseshoe, or an angular shape, may be used and are considered to be within the scope of the presently disclosed subject matter. The pad 402 is stabilized and attached to the connector 104R by the pad stabilizer 404. The pad stabilizer envelops at least a portion of the pad 402, though the surface of the pad 402 that is designed to be placed in contact with the skin or other surface to be measured or detected has preferably little to no material. In another example, one or more of the pads, and the pads themselves, may be constructed of magnetic conductors (such as carbon) that may be advantageously used in applications such as magnetic resonance imaging.

The pad stiffener 406 is used to stiffen or secure the electrical connection between the pad 402 and a wire 302A. A wire 302B is used by another node 102. The wire 302A is use by a measurement device to detect electrical activity the subject being studied (the passive configuration) or, in an alternative configuration, deliver electrical energy (the active configuration). For example, in a passive configuration, the node 402 may be used to detect electrical activity from a subject being studied. In the active configuration, the node 402 may receive enough electrical energy from the wire 302A to allow for the imaging of a portion of the body by stimulating the subject with electrical signals. For example, a body part may be imaged by deploying the node 102J, applying a current through the wire 302A into the pad 402, recording potentials, and reconstructing an image from the potentials of the node 102J and other nodes 102.

The pad 402 of the node 102J further includes a passing hole 408. The passing hole 408 is an opening through the pad 402 and is advantageously used to allow an injection through the passing hole 408 for introducing a layer of an electroconductive material between the active area of the pad 402 and a portion of skin of the subject being studied while the pad 402 is proximate to the skin of the subject being studied. A type of electroconductive material may be gel used with EEG or ECG cup electrodes, though other types of electroconductive materials may be used and are considered to be within the scope of the presently disclosed subject matter. This embodiment is particularly advantageous since it allows to introduce the electroconductive gel between the pad and the subject skin which improves the signal quality. Notably when the portion to be studied is the head, the electroconductive gel allow to create a contact between the pad and the subject skin, through the hair of the subject. The pad 402 of the node 102J further includes orifices 410. The orifices 410 may be used to provide a means for affixing the node 102J in a manner similar to the passing hole 408 or may be used to allow air to escape when the node 102J is affixed, among other uses. The passing hole 408 may also be used to determine if sufficient gel or cream is dispensed, as the cream or gel may leak through the passing hole 408 when a sufficient amount is used. It should be noted that the node 102J may include more or fewer orifices 410 and more passing holes 408 or no passing holes 408. In alternative designs, this passing hole 408 is not present, and the gel may be dispensed under the electrode by lifting it to inject the gel. According to one embodiment, the user can choose which nodes to use as electrodes by applying only to the pads 402 of those nodes the electroconductive gel. The pads without electroconductive gel, which for example are in contact with the hair of the subject, will collect low or no signal that may be further discarded by software operations.

Figure 5:
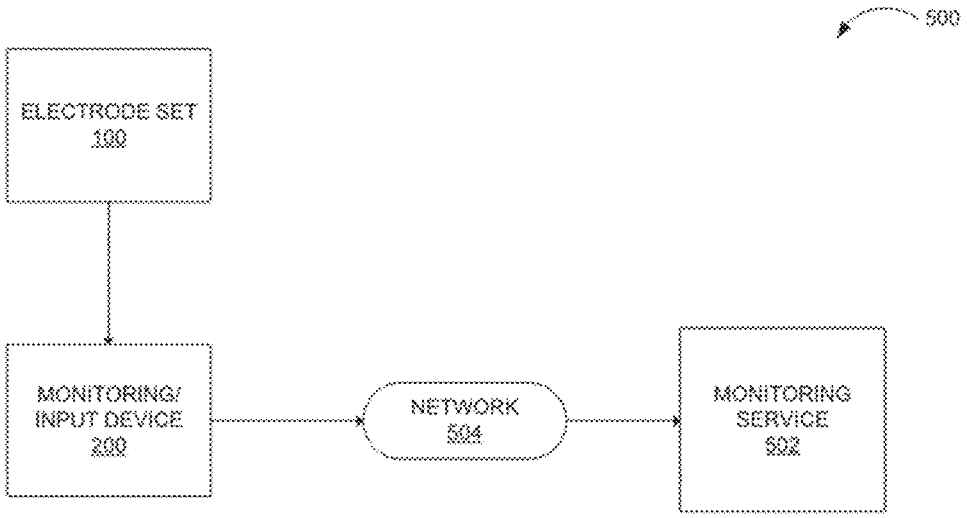
FIG. 5 is a schematic diagram depicting an electrode set system, in accordance with some examples of the present disclosure.

FIG. 5 is a schematic diagram depicting an electrode set system 500, in accordance with some examples of the present disclosure. In various examples, the electrode set 100 may be used to monitor or measure a part 202 of a body of a human. The electrode set 100 is in electrical communication with the monitoring/input device 200. As illustrated in FIG. 2, the electrode set 100 is connected to the monitoring/input device 200 by inserting the measurement leads 106A and 106B into the monitoring/input device 200. It is noted that the presently disclosed subject matter is not limited to removable measurement leads, as some configurations may include preinstalled measurement leads. These and other configurations are considered to be within the scope of the presently disclosed subject matter.

The electrode set system 500 further includes a monitoring service 502 communicatively connected to the monitoring/input device 200 through a network 504. The network 504 may be any type of network that communicatively connects the monitoring/input device 200 to the monitoring service 502, including, but not limited to, a Wi-Fi network, a local area network, or a cellular network. One of skill in the art will recognize that the systems and methods described herein can also be used with a variety of networks.

During use, the user of the electrode set 100 installs the electrode set on a body to be monitored and/or measured. The electrode set 100 is connected to the monitoring/input device 200. The monitoring/input device 200 is connected to the monitoring service 502. In some examples, the monitoring/input device 200 stores data locally while in use. In further examples, the monitoring/input device 200 transmits data to the monitoring service 502 while the electrode set 100 is in use or at anytime thereafter. In still further examples, the monitoring service 502 transmits instructions to the monitoring/input device 200 to configure the operation of the monitoring/input device 200. For example, while the monitoring/input device 200 is detecting bodily signals, the monitoring service 502 may detect an anomaly. The monitoring service 502 may send an instruction to the monitoring/input device 200 to modify its configuration from a measuring or detecting mode to an imaging mode to try to determine more information about the anomaly.

Figure 6:
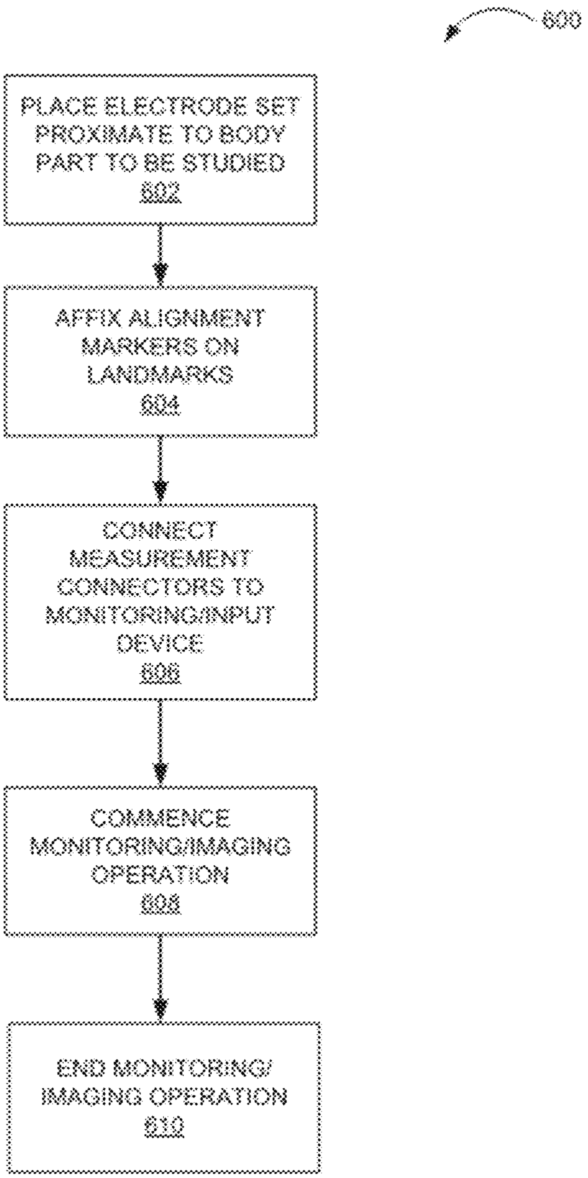
FIG. 6 is a flowchart depicting a method of using an expandable electrode set, in accordance with some examples of the present disclosure.

FIG. 6 is a flowchart depicting a process 600 of using an expandable electrode set, in accordance with some examples of the present disclosure. The process 600 and other processes described herein are illustrated as example flow graphs, each operation of which may represent a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes.

Referring to FIG. 6, the process 600 commences operation 602, where the electrode set is placed proximate to a part 202 of a human/anima/object to be studied. It should be understood that various aspects of the presently disclosed subject matter are described in terms of a human subject, though it should be understood that the presently disclosed subject matter is not limited to use on a human subject.

The process 600 continues to operation 604, where alignment markers 110 are affixed to landmarks on the part 202 or another location on the subject being studied. There may be one or more alignment markers 110 depending on the particular configuration of the electrode set 100. As the alignment markers 110 are being placed on the particular landmarks, the connectors 104 are pulled to cause a warping of at least a portion of the electrode set 100. This warping allows the electrode set 100 to transform from an undeployed, planar (or flat) configuration, to a deployed, three-dimensional confirmation that conforms to the general shape of the part 202 being monitored/imaged.

The process 600 continues to operation 606, where the measurement connectors 108 are connected to the monitoring/input device 200. In some examples, the monitoring/input device 200 may be executing a monitoring application or an imaging application (described in more detail in FIG. 8, below).

The process 600 continues to operation 608, where the monitoring or imaging of the part 202 is commenced. The process 600 thereafter ends at operation 610.

Figure 7:
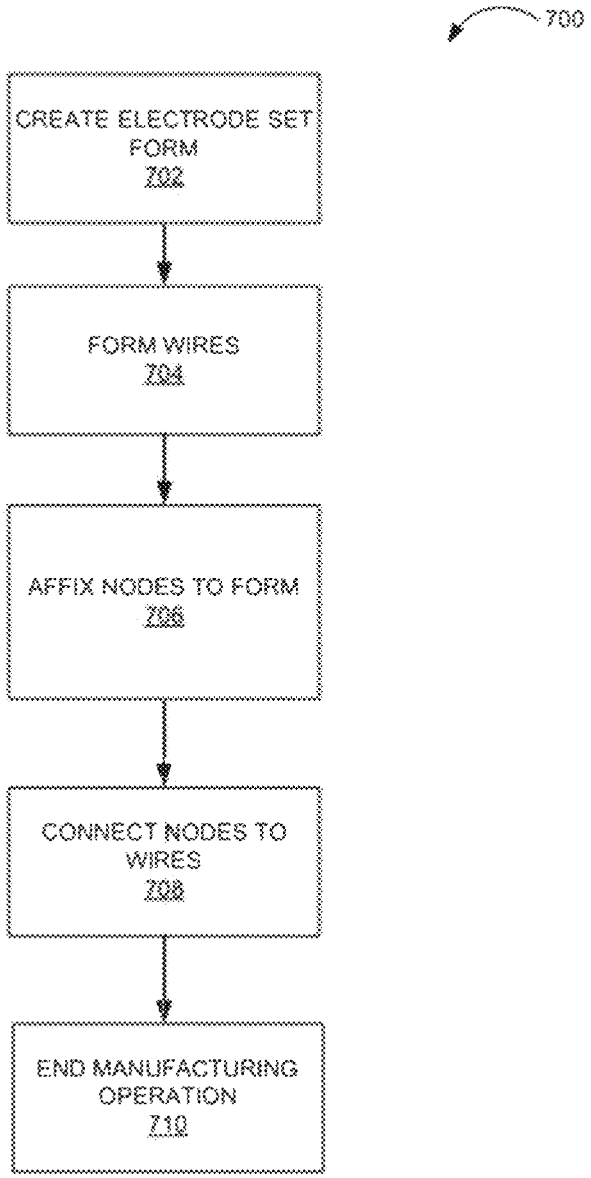
FIG. 7 is a flowchart depicting a method of manufacturing an expandable electrode set, in accordance with some examples of the present disclosure.

FIG. 7 is a flowchart depicting a process 700 for manufacturing the electrode set 100, in accordance with some examples of the present disclosure.

The process 700 commences at operation 702, where the electrode set 100 form is created. The form may be made using various processes using various materials. The form is the shape of the electrode set 100 structure. For example, in FIG. 1, the form includes the shape associated with the connectors 104, the alignment markers 110, and the like. In one example, the form is cut from a planar layer of a base material such as polyimide. The base layer can be an insulative or partially conductive layer of material upon which other materials can be placed. In some examples, the form comprises a single sheet of material, and in other examples, the form is constructed from two or more separate pieces of material. In some examples, the form may be multiple layers of material. It should be noted that instead of operation 702 being performed in the beginning, operation 702 may be performed after or before various other operations of process 700.

The process 700 continues at operation 704, where wires 302 are plated onto the form (or the base material if performed before operation 702). The wires 302 connect individual nodes 102 to the monitoring/input device 200 through the measurement leads 106A and 106B. The wires 302 may be formed using various plating or deposition technologies. The wires 302 may be formed from various conductive or semiconductive materials such as, but not limited to, copper, aluminum, gold, silver, and alloys thereof. The thickness of the wires 302 may vary, but in some examples, are between 0.3 and 0.5 μm.

The process 700 continues to operation 706, where the nodes 104 are affixed to the form. The nodes may be preformed metal discs of various conductive or semiconductive materials such as, but not limited to, copper, aluminum, gold, silver, and alloys thereof.

The process 700 continues to operation 708, where the nodes 104 are affixed to the wires 302 thru the pad stiffener 406 for each of the nodes 102. The pad stiffeners 406 may be formed from various materials, including polyimide or other polymers that provide sufficient structure support for the connection between the wires 302 and the pads 402.

The process 700 ends at operation 710.

Figure 8:
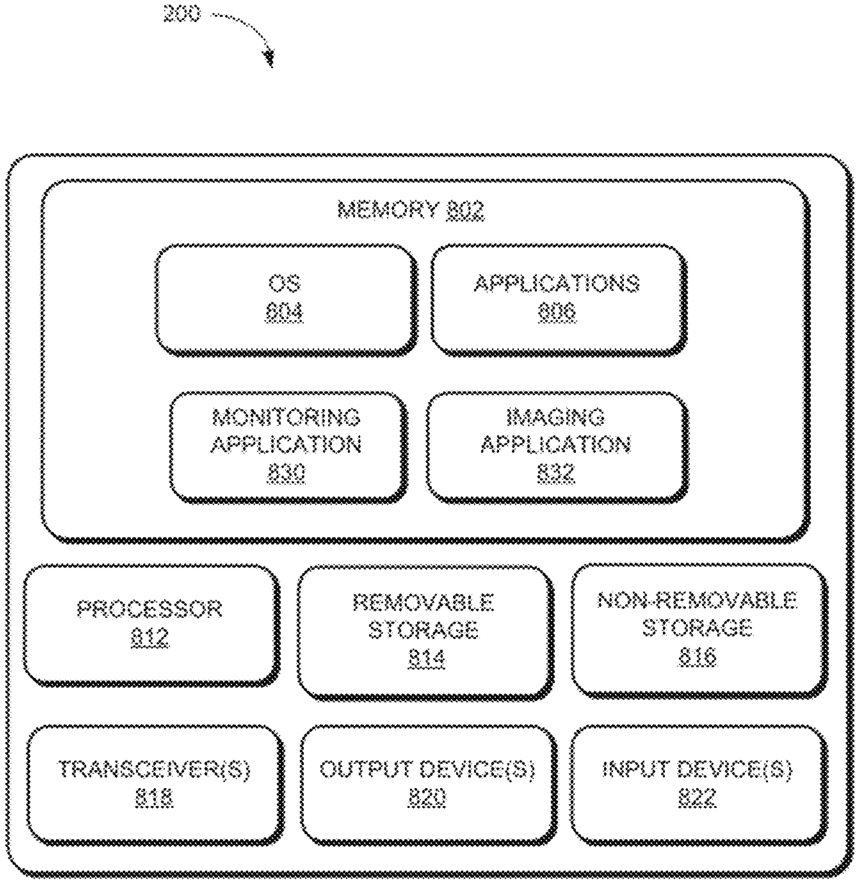
FIG. 8 is a depicts a component level view of a monitoring/input device for use with the systems and methods described herein, in accordance with some examples of the present disclosure.

FIG. 8 monitoring/input device for use with the systems and methods described herein, in accordance with some examples of the present disclosure. FIG. 8 illustrates the monitoring/input device 200 of FIG. 2 and FIG. 5, by way of example. The monitoring/input device 200 could be any computing component capable of communicating with or on a cellular network, an internet multimedia subsystem, and/or an IP network. One of skill in the art will recognize that the systems and methods described herein can also be used with a variety of electronic devices, such as, for example, tablet computers, desktops, servers, and other network connected devices.

The monitoring/input device 200 can comprise several components to execute various above-mentioned functions. The monitoring/input device 200 can comprise memory 802 including an operating system (OS) 804 and one or more standard applications 806. The standard applications 806 can include applications to control the various components of the monitoring/input device 200. In this case, the standard applications 806 can also comprise a monitoring application 830 and an imaging application 832. The monitoring application 830 may be instantiated to control the operation of the monitoring/input device 200 for detecting signals generated from a body. The control may also include the determination of which nodes receive what signals and the storage of that data. The imaging application 832 may be instantiated to configure the monitoring/input device 200 to act as an imaging device, whereby one or more of the nodes are energized to input electrical energy. For example, if instantiated, the imaging application 832 may cause the monitoring/input device 200 to applying a current to one or more of the nodes, record potentials of nodes not receiving a current, and constructing an image from the potentials.

In this method, the monitoring/input device 200 or the monitoring service 502 (or another device) defines a subset of nodes 102 to which a current is applied. Then monitoring/input device 200 records potentials on the nodes 102 that do not receive the current. Optionally, several subsets of the nodes 102 having different patterns are defined successively and resulting potentials are recorded successively. In other words, sets of the nodes 102 are changed and the application of current is repeated with different nodes 102. The monitoring/input device 200 or the monitoring service 502 determines an image of the part 202 of the body of the subject, for instance with an image reconstruction algorithm. Such method is suitable for noninvasive imaging such as electrical impedance tomography (EIT), in absolute (a-EIT), time difference (td-EIT) or multifrequency (MF-EIT) mode. Various part of the body may be imaged with this method, in particular lung, muscles, breast, cervix, brain, bladder, or limb. This method may be used for imaging volume variation of body parts, in particular under blood flow or perfusion.

In another example, one or more of the pads 402 of the nodes 102 may be replaced by other types of electromagnetic energy emitters, such as an infrared, visible, or near infrared light emitting diode (LED). In some examples, as explained above, the nodes 102 may be emitters, sensors, or a coupling of an emitter/sensor. For example, a coupled emitter/sensor may be used to acquire a signal in the case of a non-self-emitted physiologic signal. The near infrared emitters can be used in processes such as near infrared spectroscopy or optical coherence tomography. The standard applications 806 can also include one or more functions or operations as those described in FIGS. 1-8, above. In some further examples, one or more of the nodes 102 may be ultrasonic transducers coupled to be used in applications such as echography applications. As used herein, an ultrasonic transducer may be a transmitter, receiver, and/or transceiver.

The monitoring/input device 200 may also comprise one or more processors 812 and one or more of removable storage 814, non-removable storage 816, transceiver(s) 818, output device(s) 820, and input device(s) 822. In various implementations, the memory 802 can be volatile (such as random-access memory (RAM)), non-volatile (such as read only memory (ROM), flash memory, etc.), or some combination of the two. The memory 802 may be used to store various data received from the electrode set 100 and/or data received from the monitoring service 502 through the network 504.

The memory 802 can also include the OS 804. The OS 804 contains the modules and software that support basic functions, such as scheduling tasks, executing applications, and controlling peripherals. In some examples, the OS 804 can enable the monitoring application 830, the imaging application 832, and provide other functions, as described above, via the transceiver(s) 818. The OS 804 can also enable the monitoring/input device 200 to send and retrieve other data and perform other functions. It should be noted that one or more functions of the presently disclosed subject matter may be executed by other systems than the OS 804, such as firmware/FPGA/ASIC.

The monitoring/input device 200 can also comprise one or more processors 812. In some implementations, the processor(s) 812 can be a central processing unit (CPU), a graphics processing unit (GPU), both CPU and GPU, or any other processing unit such as an application-specific integrated circuit (ASIC) or Field Programmable Gate Arrays (FPGA), by way of example and not by way of limitation. The monitoring/input device 200 may also include additional data storage devices (removable and/or non-removable) such as, for example, magnetic disks, optical disks, or tape. Such additional storage is illustrated in FIG. 8 by removable storage 814 and non-removable storage 816.

Non-transitory computer-readable media may include volatile and nonvolatile, removable and non-removable tangible, physical media implemented in technology for storage of information, such as computer readable instructions, data structures, program modules, or other data. The memory 802, removable storage 814, and non-removable storage 816 are all examples of non-transitory computer-readable media. Non-transitory computer-readable media include, but are not limited to, RAM, ROM, electronically erasable programmable ROM (EEPROM), flash memory or other memory technology, compact disc ROM (CD-ROM), digital versatile discs (DVD) or other optical storage, magnetic cassettes, magnetic tape, magnetic disk storage or other magnetic storage devices, or any other tangible, physical medium which can be used to store the desired information and which can be accessed by the monitoring/input device 200. Any such non-transitory computer-readable media may be part of the monitoring/input device 200 or may be a separate database, databank, remote server, or cloud-based server.

In some implementations, the transceiver(s) 818 include any transceivers known in the art. In some examples, the transceiver(s) 818 can include wireless modem(s) to facilitate wireless connectivity with other components (e.g., between the monitoring/input device 200 and the network 504), the Internet, and/or an intranet, as well as wireless network adapters or other capable equipment.

The transceiver(s) 818 may also include one or more radio transceivers that perform the function of transmitting and receiving radio frequency communications via an antenna (e.g., Wi-Fi or Bluetooth®). In other examples, the transceiver(s) 818 may include wired communication components, such as a wired modem or Ethernet port, for communicating via one or more wired networks. The transceiver (s) 818 can enable the monitoring/input device 200 to download files, access web applications, and provide other communications associated with the systems and methods, described above.

In some implementations, the output device(s) 820 include any output devices known in the art, such as a display (e.g., a liquid crystal or thin-film transistor (TFT) display), a touchscreen, speakers, a vibrating mechanism, or a tactile feedback mechanism. Thus, the output device(s) can include a screen, or display. The output device(s) 820 can also include speakers, or similar devices, to play sounds or ringtones when an audio call or video call is received. Output device(s) 820 can also include ports for one or more peripheral devices, such as headphones, peripheral speakers, or a peripheral display.

In various implementations, input device(s) 822 include any input devices known in the art. For example, the input device(s) 822 may include one or more components of the electrode set 100. In another example, the input device(s) 822 may include a camera, a microphone, or a keyboard/keypad. The input device(s) 822 can include a touch-sensitive display or a keyboard to enable users to enter data and make requests and receive responses via web applications (e.g., in a web browser), make audio and video calls, and use the standard applications 806, among other things. For example, the monitoring/input device 200 may be a cellular telephone having input ports capable of receiving data from the electrode set 100. The touch-sensitive display or keyboard/keypad may be a standard push button alphanumeric multi-key keyboard (such as a conventional QWERTY keyboard), virtual controls on a touchscreen, or one or more other types of keys or buttons, and may also include a joystick, wheel, and/or designated navigation buttons, or the like.

The presently disclosed examples are considered in all respects to be illustrative and not restrictive. The scope of the disclosure is indicated by the appended claims, rather than the foregoing description, and all changes that come within the meaning and range of equivalents thereof are intended to be embraced therein.

The invention claimed is:

1. An electrode set adapted to be positioned on a subject for electrophysiological signal monitoring, the electrode set comprising:

a base planar substrate comprising:

a plurality of nodes each comprising a pad for receiving electromagnetic energy from a portion of a part being studied, wherein each nodes are arranged in a longitudinal series of nodes aligned along a longitudinal line, and a transverse series of nodes aligned along a transverse line extending transversally to the longitudinal line, wherein the longitudinal series of nodes including opposite end nodes spaced apart in a longitudinal direction and the transverse series of nodes including opposite end nodes spaced apart in a transverse direction transversal to the longitudinal direction;

a plurality of connectors each presenting a shape selected from a sinusoidal shape, a spiral shape, a double spiral shape, a U-shape, or an angular shape and a predetermined elastic force and connecting two adjacent nodes of the plurality of nodes, wherein each of the plurality of nodes is connected to an adjacent node along the transverse series of nodes via one connector of the plurality of connectors and another adjacent node along the longitudinal series of nodes via another connector of the plurality of connectors; and a wire disposed on each of the plurality of connectors and configured to electrically connect its respective pad of the plurality of pads to a measurement lead, wherein the measurement lead terminates at a measurement connector to be inserted into a monitoring/input device;

wherein the electrode set further comprises at least two longitudinal alignment markers each affixed to a marker connector of the plurality of connectors which extends from its respective end node of the longitudinal series of nodes, and at least two transverse alignment markers each affixed to a marker connector of the plurality of connectors which extends from its respective end node of the transverse series of nodes, the longitudinal and transverse alignment markers being configured to be removably affixed to a landmark on the subject of the part being studied and once affixed to the landmark of the subject, exert a pull force on the nodes closest to the at least two longitudinal alignment markers and the at least two transverse alignment markers through the marker connectors in order to transfer the pull force in directions of two or more force vectors to the plurality of nodes, and to shift the electrode set from a planar undeformed state into a non-planar deployed state;

wherein each connector of the plurality of connectors along the longitudinal series of nodes stretches along the longitudinal line from a first distance to a second distance when the pull force is applied; and wherein each connector of the plurality of connectors along the transverse series of nodes stretches along the transverse line from a third distance to a fourth distance when the pull force is applied.

2. The electrode set according to claim 1, the base substrate further comprising a pad stiffener affixed to each of the plurality of nodes.

3. The electrode set according to claim 1, wherein the base substrate is formed from a plastic substrate, polyimide, polyethylene, polyether ether ketone (PEEK), or a non-conductive polyester or polymer.

4. The electrode set according to claim 1, wherein each of the pads comprises conductive or semi-conductive materials.

5. The electrode set according to claim 1, wherein each of the pads comprises copper, aluminum, stainless steel, gold, silver, or alloys thereof.

6. The electrode set according to claim 1, wherein the wire comprises copper, aluminum, stainless steel, gold, silver, or alloys thereof.

7. The electrode set according to claim 1, wherein each of the pads comprises a passing hole that allow for an injection of an electroconductive material enhancing electrical contact with skin.

8. A method of measuring electrophysiological signals of a part of a subject, the method comprising:

placing an electrode set, according to claim 1, proximate to the part to be measured;

affixing the at least two longitudinal alignment markers and the at least two transverse alignment markers to a respective landmark on the subject of the part being studied;

connecting the measurement lead to the monitoring/input device; and initiating a monitoring application in the monitoring/input device to commence measuring the electrophysiological signals of the part of the subject.

9. The method according to claim 8, further comprising injecting an electroconductive, sonic, or light transmitting material through a respective hole of each pad of the plurality of nodes.

10. A sensor set system comprising:

a sensor set according to claim 1, wherein the monitoring/input device is configured to receive data of electrophysiological signals or transmitting instructions to the monitoring/input device.

* * * * *